United States Patent [19]
Davis et al.

[11] Patent Number: 5,853,984
[45] Date of Patent: Dec. 29, 1998

[54] USE OF NUCLEIC ACID LIGANDS IN FLOW CYTOMETRY

[75] Inventors: Ken Davis, Los Altos, Calif.; Sumedha Jayasena; Larry Gold, both of Boulder, Colo.

[73] Assignee: NeXstar Pharmaceuticals, Inc., Boulder, Colo.

[21] Appl. No.: 479,729

[22] Filed: Jun. 7, 1995

Related U.S. Application Data

[63] Continuation-in-part of Ser. No. 964,624, Oct. 21, 1992, Pat. No. 5,496,938, Ser. No. 199,507, Feb. 22, 1994, Pat. No. 5,472,841, Ser. No. 234,997, Apr. 28, 1994, Pat. No. 5,683,867, and Ser. No. 714,131, Jun. 10, 1991, Pat. No. 5,475,096, which is a continuation-in-part of Ser. No. 536,428, Jun. 11, 1990, abandoned.

[51] Int. Cl.⁶ .......................... C12Q 1/68; G01N 33/566; C07H 21/02; C07H 19/04
[52] U.S. Cl. .............................. 435/6; 436/501; 536/23.1; 536/26.6
[58] Field of Search ................................ 435/6; 436/501; 536/26.6, 23.1

[56] References Cited

U.S. PATENT DOCUMENTS

| | | | |
|---|---|---|---|
| 4,599,307 | 7/1986 | Saunders et al. | 436/63 |
| 4,704,891 | 11/1987 | Recktenwald et al. | 73/1 R |
| 4,727,020 | 2/1988 | Recktenwald | 435/6 |
| 5,270,163 | 12/1993 | Gold et al. | 435/6 |

FOREIGN PATENT DOCUMENTS

| | | |
|---|---|---|
| 2 183 661 | 6/1987 | United Kingdom . |
| WO/89/06694 | 7/1989 | WIPO . |
| WO 92/14843 | 9/1992 | WIPO . |
| WO 93/05182 | 3/1993 | WIPO . |
| WO 94/01448 | 1/1994 | WIPO . |

OTHER PUBLICATIONS

Joyce (1989) Gene 82:83.
Joyce and Inoue (1989) Nucleic Acids Research 17:711.
Ellington and Szostak (1990) Abstract of papers presented at the 1990 meeting on RNA Processin, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Haynes et al. (1988) Cytometry Supplement 3:7.
Chihara, et al., Induction of CD23, CD25, and CD4 Expression on an Eosinophilic Cell Line (Eol–3) by interleukin–3 (IL–3), Granulocyte–macrophage Colony–stimulating Factor (GM–CSF) and Interleukin–5 (IL–5), Eur. Cytokine Network, 3:53–61 (1992).
Zhao et al. Comparison of Cellular Binding and Uptake of Antisense Phosphodiester, Phosphorothioate, and Mixed Phosphorothioate and Methylphosphonate Oligonucleotides: Anitsense Research and Development 3:53–66, 1993.

Primary Examiner—Stephanie W. Zitomer
Assistant Examiner—Joyce Tung
Attorney, Agent, or Firm—Swanson & Bratschun LLC

[57] ABSTRACT

This invention discloses the use of high-affinity oligonucleotide ligands in flow cytometry diagnostic applications. Specifically, DNA ligands having one or more fluorophore molecules attached are disclosed which are useful in flow cytometry.

14 Claims, 4 Drawing Sheets

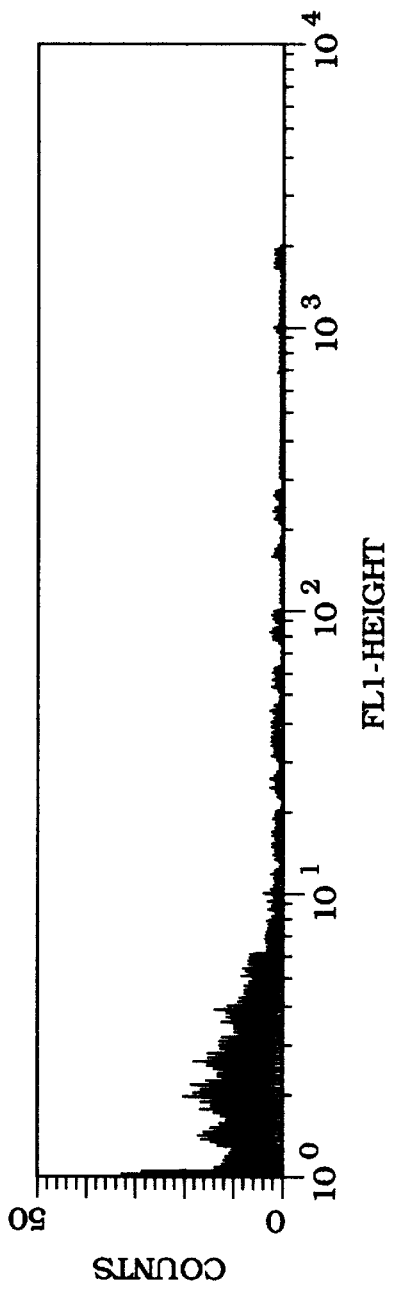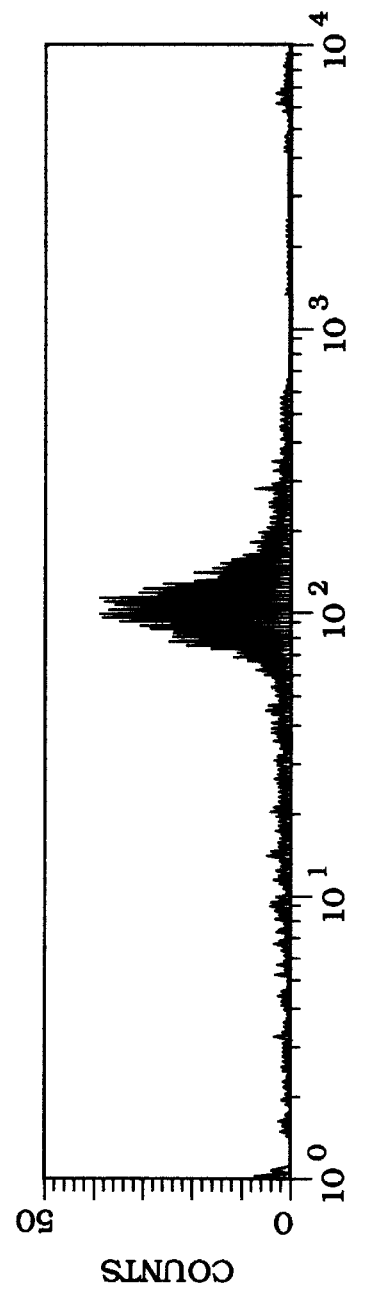

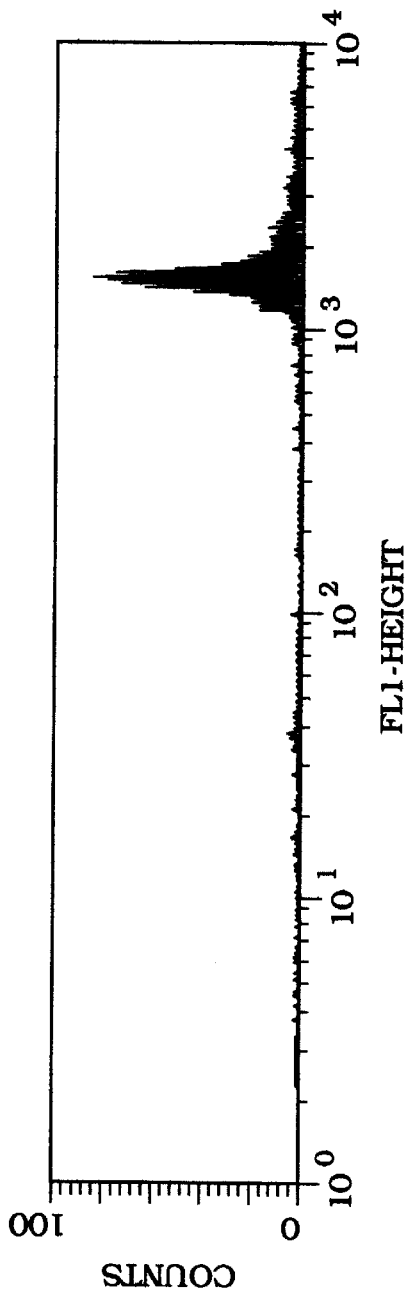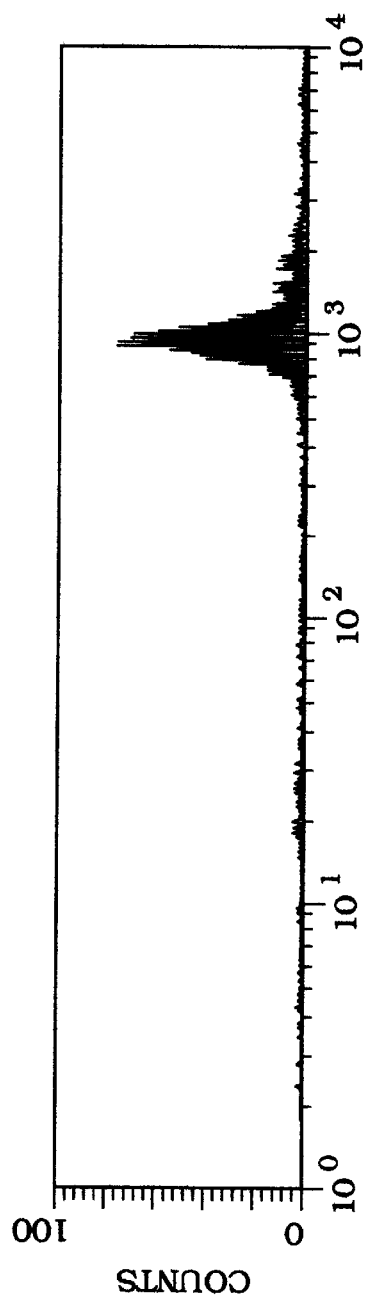
FIG. 1C
FIG. 1D

USE OF NUCLEIC ACID LIGANDS IN FLOW CYTOMETRY

RELATED APPLICATIONS

This application is a Continuation-in-Part of U.S. patent application Ser. No. 07/714,131, filed Jun. 10, 1991, entitled "Nucleic Acid Ligands" now issued as U.S. Pat. No. 5,475,096, which is a Continuation-in-Part of U.S. patent application Ser. No. 07/536,428, filed Jun. 11, 1990, entitled "Systematic Evolution of Ligands by Exponential Enrichment", now abandoned, and U.S. patent application Ser. No. 07/964,624, filed Oct. 21, 1992, entitled Nucleic Acid Ligands to HIV-RT and HIV-1 Rev now issued as U.S. Pat. No. 5,496,930, U.S. patent application Ser. No. 08/199,507, filed Feb. 22, 1994, entitled Methods for Identifying "Nucleic Acid Ligands of Human Neutrophil Elastase" now issued as U.S. Pat. No. 5,472,841 and U.S. patent application Ser. No. 08/234,997, filed Apr. 28, 1994, entitled "Systematic Evolution of Ligands by Exponential Enrichment: Blended SELEX" now issued as U.S. Pat. No. 5,683,867.

FIELD OF THE INVENTION

Described herein are methods for using nucleic acid ligands in flow cytometry applications. A nucleic acid ligand is a non-naturally occurring nucleic acid having a specific binding affinity for a target. A nucleic acid ligand can be directed to any target in any format that is suitable for use in flow cytometry. In a preferred embodiment, the nucleic acid ligands bind cell surface proteins with high affinity and specificity. In another embodiment, the nucleic acid ligands bind intracellular proteins. In yet another embodiment, the nucleic acid ligands bind to targets in a substance which has been coated on a solid support, such as a bead. The method utilized herein for identifying and preparing said nucleic acid ligands is called SELEX, an acronym for Systematic Evolution of Ligands by EXponential enrichment. The invention includes high-affinity nucleic acid ligands having attached one or more fluorophore molecules which may be employed in flow cytometric methodologies.

BACKGROUND OF THE INVENTION

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment", now abandoned, U.S. patent application Ser. No. 07/714,131, filed Jun. 10, 1991, entitled "Nucleic Acid Ligands" now issued as U.S. Pat. No. 5,475,096, U.S. patent application Ser. No. 07/931,473, filed Aug. 17, 1992, entitled Methods for Identifying "Nucleic Acid Ligands", now U.S. Pat. No. 5,270,163 (see also PCT/US91/04078) (WO91/19813), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure" now abandoned (See, U.S. Pat. No. 5,707,796, describes the use of SELEX in conjunction with gel electrophoresis to select nucleic acid molecules with specific structural characteristics, such as bent DNA. U.S. patent application Ser. No. 08/123,935, filed September 17, 1993, entitled "Photoselection of Nucleic Acid Ligands", now abandoned, describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine" now abandoned (See, U.S. Pat. No. 5,580,737, describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX" now abandoned (See, U.S. Pat. No. 5,567,588, describes a SELEX-based method which achieves highly efficient partitioning between oligonucleotides having high and low affinity for a target molecule. U.S. patent application Ser. No. 07/964,624, filed Oct. 21, 1992, entitled Nucleic Acid Ligands to HIV-RT and HIV-1 Rev now issued as U.S. Pat. No. 5,496,938 describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX" now issued as U.S. Pat. No. 5,705,337, describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides" now abandoned (See. U.S. Pat. No. 5,660,985), that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nucleosides by Intramolecular Nucleophilic Displacement", describes novel methods for producing novel 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" now issued as U.S. Pat. No.

5,637,459, and U.S. patent application Ser. No. 08/234,997, filed Apr. 28, 1994, entitled "Systematic Evolution of Ligands by Exponential Enrichment: Blended SELEX" now issued as U.S. Pat. No. 5,683,867, respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

Without question, the SELEX process is very powerful. The nucleic acid ligands obtained by the SELEX process have the ability to act in many capacities. One of the capacities that nucleic acid ligands possess is the ability to bind specifically to a target.

Specific and high affinity molecular recognition is critical for diagnostics. Until recently, engineering of molecules that recognize targets has been mainly limited to proteins. Protein molecules that recognize a specific target have typically been generated as antibodies. As a result, antibodies have played a central role in the development of analytical and separation methods that are currently being used. The methods which primarily use antibodies include, immunometric assays such as enzyme-linked immunosorbent assays (ELISAs), radioimmunoassays, flow cytometry diagnostics, blotting applications, anisotropy, membrane assays, biosensors, etc.

Flow cytometry, the measurement of cells in a moving liquid stream, is well established as a valuable analytical tool in research laboratories and clinical settings (Haynes, Cytometry Supplement, (1988) 3:7–17). Flow cytometry is unique, as compared to other diagnostic techniques, in its capability to perform simultaneous multiparameter analysis and to separate (or sort) unique cell populations from heterogeneous mixtures.

Cellular analysis generally comprises the analyses of cells. This analysis can include visual inspection via light or fluorescent light microscopy and can further include automated analysis by means of image analysis and flow cytometry. In each instance, cells are stained with one or more labeled cell surface markers and then examined. Examination of the cells and their markers can provide information regarding the lineage of the cell and/or its maturational stage.

Flow cytometry comprises a well known methodology for identifying and distinguishing between different cell types in a non-homogeneous sample. The sample may be drawn from a variety of sources such as blood, lymph, urine, or may be derived from suspensions of cells from hard tissues such as kidney or liver. In the flow cytometer, cells are passed substantially one at a time through one or more sensing regions where each cell is interrogated by an energy source. The energy source generally comprises means that emits light of a single wavelength such as that provided by a laser (e.g., He/Ne or argon) or a mercury arc lamp with appropriate filters.

In series with the sensing region, various light collection means, such as photomultiplier tubes, are used to gather light that passes through each cell (generally referred to as forward light scatter), light that is reflected orthogonal to the direction of the flow of the cells through the sensing region (generally referred to as orthogonal light scatter) and one or more light collection means to collect fluorescent light that may be emitted from the cell as it passes through the sensing region and is interrogated by the energy source.

Flow cytometers further comprise data recording and storage means, such as a computer, wherein separate channels record and store the light scattered and fluorescence emitted by each cell as it passes through the sensing region. By plotting orthogonal light scatter versus forward light scatter, one can distinguish between granulocytes, monocytes and lymphocytes in a population of leukocytes. By electronically (or manually) gating on only lymphocytes using light scatter, for example, and by the use of appropriate immunofluorescent markers, such as monoclonal antibodies labeled with fluorochromes of different emission wavelength, one can further distinguish between cell types within the lymphocyte population (e.g., between T helper cells and T cytotoxic cells). U.S. Pat. Nos. 4,727,020, 4,704,891 and 4,599,307 describe the arrangement of the various components that comprise a flow cytometer and also the general principles of its use.

Flow analysis of particles has been employed in the determination of characteristics of individual particles. Characteristics that can be determined by flow cytometry include, but are not limited to, size, shape, granularity, and binding properties. Such analysis is most useful in analyzing characteristics of cells for the collection of information which would be useful in areas of research, hemotology, immunology and the like. One may be interested, for example, in determining specific characteristics of individual cells so that the cells may be classified, identified, quantified and then sorted for further investigations, analyses or other activities. There are a number of well-known cell sorters available at present using flow cytometry techniques for the analysis of characteristics of individual cells and the subsequent sorting of those cells of particular interest. One such fluorescence-activated cell sorter is known as the FACS Vantage™ cell sorter, sold by Becton Dickinson Immunocytometry Systems, San Jose, Calif.

In addition to antibodies, oligonucleotides are also being used in diagnostics, but in a different manner. Sequence information of oligonucleotide probes is used to specifically target genomic complementary base sequences in techniques such as Southern blotting, in situ hybridization and polymerase-based amplifications. However, information stored in an oligonucleotide is not being generally used to detect non-nucleic acid molecules. The information content (linear sequence) of nucleic acids relies on Watson/Crick base pairing and can only discriminate among DNAs. However, relying on structural content (three-dimensional structures), nucleic acid ligands can be used in diagnostic applications for any type of target. Before SELEX, the structural content of nucleic acids was essentially not appreciated and there was no way to utilize the structural capabilities of nucleic acids.

The use of nucleic acid ligands in diagnostic assays which were previously dependent on antibody recognition has not been previously demonstrated. This application discloses a method for using SELEX-derived high affinity oligonucleotide ligands in flow cytometry.

SUMMARY OF INVENTION

The present invention includes the use of nucleic acid ligands in flow cytometry applications. More specifically, the nucleic acid ligands contain one or more fluorescent molecules and are employed in flow cytometry methodologies.

The present invention includes a method for detecting the presence of a target compound in a substance which may contain said target compound comprising a) mixing said substance which may contain said target compound with a fluorophore labelled nucleic acid ligand which is capable of binding to said target molecule; b) optionally removing any unbound nucleic acid ligand from said mixture; and c) analysis by flow cytometry and determining whether said labelled nucleic acid ligand is bound to said target. The target in the substance may be presented in a number of different formats. The target may be a cell surface protein or intracellular protein presented in the context of the cell in a homogeneous or heterogeneous environment. The target may also be a soluble analyte in a substance which has been coated on a solid support, such as a bead.

The present invention also includes an embodiment wherein the target is a soluble analyte in a substance that is first captured on a solid support by a capture molecule, is second detected by a detector molecule, and is third analyzed by flow cytometry to determine whether said target is in said substance. This embodiment provides a method for detecting the presence of a target compound in a substance which may contain said target compound comprising a) immobilizing on a particulate solid support a capture molecule capable of binding to said target molecule; b) exposing a substance which may contain said target compound to said capture molecule; c) adding to said capture molecule:target molecule complex a fluorophore-labelled detector molecule capable of binding to said target molecule; and d) detecting said capture molecule:target molecule:detector molecule complex by flow cytometry; wherein said capture molecule, detector molecule or both are a nucleic acid ligand to said target molecule.

BRIEF DESCRIPTION OF THE FIGURES

FIGS. 1A–1D shows the results of flow cytometric analysis of fluoresceinated DNA and anti-HNE antibody binding to HNE coated beads. FIG. 1A shows autofluorescence of HNE coated beads; FIGS. 1B and 1C show binding of DNA-3F (FIG. 1B) and DNA-LNK-3F (FIG. 1C) at 1 $\mu$M concentration; and FIG. 1D shows anti-HNE monoclonal antibody binding at 0.2 $\mu$M concentration.

DETAILED DESCRIPTION OF THE INVENTION

Figure 2:
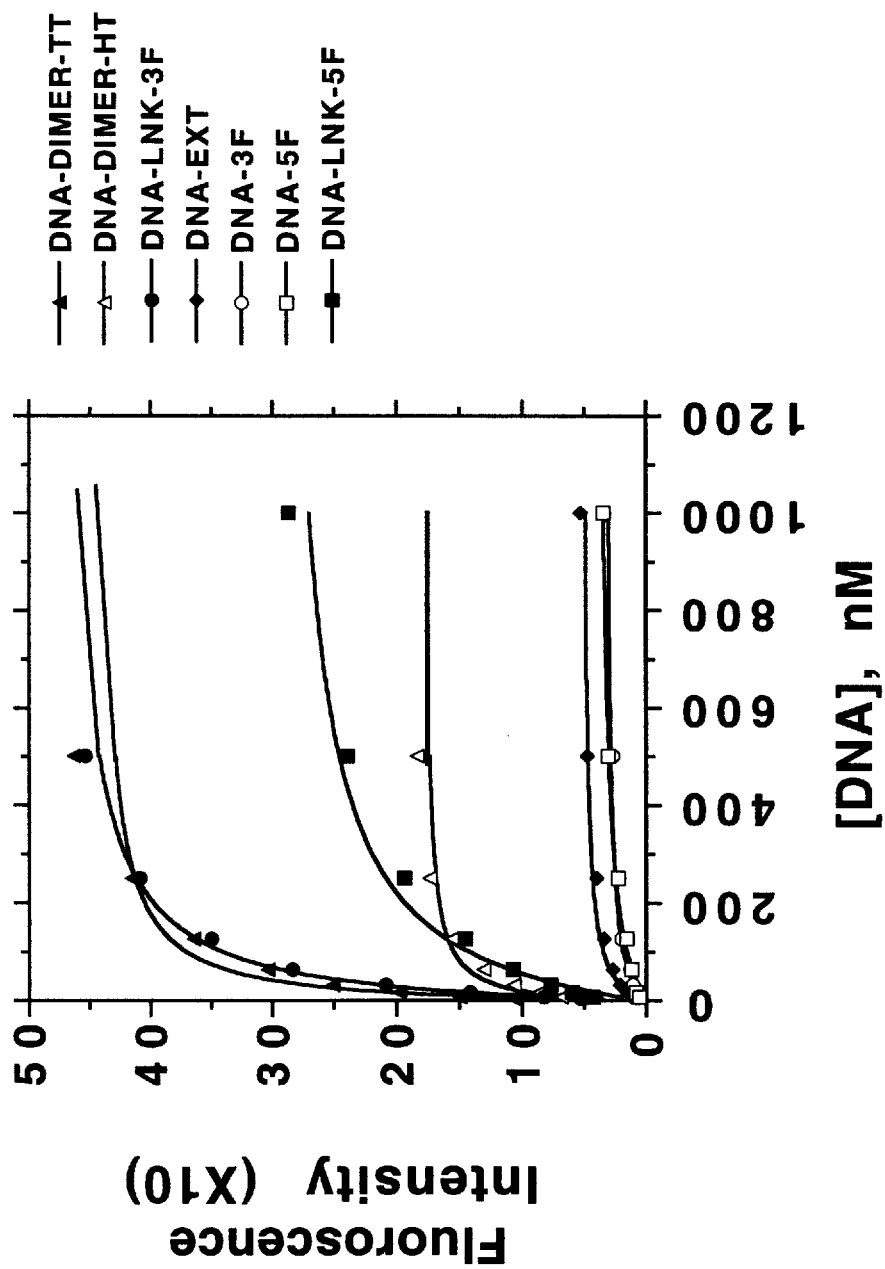
FIG. 2 indicates binding affinities of various DNA constructs.

This application describes the use in flow cytometry of high-affinity nucleic acid ligands to various targets. Nucleic acid ligand is defined herein as a non-naturally occurring nucleic acid having a specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. In the preferred embodiments, the nucleic acid ligand is a single stranded nucleic acid ligand.

In the preferred embodiment, the nucleic acid ligands are identified through the method known as SELEX. SELEX is described in U.S. patent application Ser. No. 07/536,428, entitled *Systematic Evolution of Ligands by EXponential Enrichment*, now abandoned, U.S. patent application Ser. No. 07/714,131, filed Jun. 10, 1991, entitled *Nucleic Acid Ligands*, now issued as U.S. Pat. No. 5,475,096, U.S. patent application Ser. No. 07/931,473, filed Aug. 17, 1992, entitled Methods for Identifying *Nucleic Acid Ligands*, now U.S. Pat. No. 5,270,163, (see also PCT/US91/04078) (WO91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with a lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate an enriched candidate mixture. The SELEX Patent Applications also describe ligands obtained to a number of target species, including both protein targets where the protein is and is not a nucleic acid binding protein.

SELEX provides high affinity ligands of a target molecule. This represents a singular achievement that is unprecedented in the field of nucleic acids research. Affinities of SELEX-derived nucleic acid ligands often lie in the same range observed with structurally large monoclonal antibodies.

Particularly preferred methods for identifying nucleic acid ligands which are useful in the present invention are described in copending U.S. patent applications Ser. No. 08/434,425 filed May 3, 1995, entitled "Systematic Evolution of Ligands by Exponential Enrichment: Tissue SELEX", and U.S. patent application Ser. No. 08/433,124, filed May 3, 1995, entitled "Nucleic Acid Ligands of Tissue Target", which are herein specifically incorporated by reference in their entirety.

Until recently, the design and production of biopolymers capable of molecular recognition has been mainly limited to proteins (antibodies). However, SELEX allows the identification of nucleic acid sequences that recognize target molecules with high affinity and specificity. This process is faster than the generation of monoclonal antibodies and does not require the use of animals as required to generate antibodies. Once the sequence of a high-affinity ligand is identified, the material can be chemically synthesized in large quantities. This is a definite advantage over processing and storage of antibody-producing cell lines.

Moreover, specific and high-affinity nucleic acid ligands can be generated for targets that are not readily immunogenic. This adds a new dimension to the types of information that can be gained from this diagnostic application. Clearly, target compounds that have never before been diagnosed due to lack of appropriate diagnostic tools can now be diagnosed using this new procedure.

The nucleic acid ligands of the present invention offer additional advantages over antibodies. Nucleic acid ligands may have a greater specificity for target compounds than the specificity exhibited by conventional antibodies as demonstrated in U.S. patent application Ser. No. 09/134,028, filed Oct. 7, 1993, entitled "High Affinity Nucleic Acid Ligands the Discriminate Between Theophylline and Caffeine," abandoned in favor of U.S. patent application Ser. No. 08/443,957, now U.S. Pat. No. 5,580,737, which is herein incorporated by reference. Whereas antibodies generally have multiple binding sites, only two of which are specific for a target compound, the entire molecule of the nucleic acid ligand may be utilized for the binding of a target compound. The nucleic acid ligands of the invention are identified and prepared to contain a single specific binding site. Thus, there is potentially far less nonspecific binding of nontarget compounds when nucleic acid ligands are utilized in flow cytometry. This provides a more reliable detection signal for the presence of target compound.

In vitro selection-amplification technology has produced oligonucleotide ligands that bind a variety of target molecules with high affinity and specificity. These oligonucleotide ligands can be used in diagnostics. In diagnostic applications molecular recognition is coupled to detection which is usually accomplished by attaching different reporter groups to a ligand. The reporter groups are molecular species exemplified generally by fluorophores, radioisotopes, enzymes, and the like. Thus, to be useful in such applications oligonucleotides must tolerate the attachment of other molecular species without losing their affinity and specificity. The oligonucleotides can be easily modified to include other useful moieties such as fluorophores such as fluorescein, radioisotopes such as phosphorous 32 ($^{32}P$), steroids such as cholesterol or digoxygenin, biotins and peptides. The various modifications allow the choice of an available reporter system. In fact, it is generally possible to covalently or even non-covalently link the oligonucleotide directly to a reporter fluorophore.

The use of nucleic acid ligands in flow cytometry may offer certain added benefits. Unlike antibodies, oligonucleotides derivatized with various reporter groups, such as fluorophores, at defined positions can be obtained by direct chemical synthesis of the oligomer. Functional groups that react with proteins and other molecules can also be placed in an oligonucleotide chain during synthesis. In contrast to antibody labeling, the reporter group attachment sites on an oligonucleotide are easier to control.

One of the biggest advantages is that the relatively small oligonucleotides of known sequence can easily be replicated in many laboratories and, unlike antibodies, will have the same binding properties.

An additional advantage of utilizing nucleic acid ligands in flow cytometry is that certain target compounds will bind to nucleic acid ligands, but will not bind to antibodies. Examples of such compounds are small molecules that cannot be conjugated to larger proteins to illicit an immune response in mice or rabbits such as glucose, and catecholamines such as epinephrine, norepinephrine and $\alpha$-3-deoxy-D-manno-octulosonic acid (a trisaccharide specific for Chlamydia organisms).

Furthermore, due to the smaller size (compared to antibodies), nucleic acid ligands are expected to be effective in intracellular staining, i.e., nucleic acid ligands can be used in detecting the expression of target molecules at the cellular level. Although most studies with flow cytometry are based on staining of cell surface proteins, detection of intracellular protein levels by intracellular staining is gaining popularity. Currently, this is being accomplished by antibodies. The small size of SELEX-derived nucleic acid ligands (<20 kD) offers an additional advantage over structurally large antibodies (~160 kD) to be used as intracellular probes. The binding of the Fc region of antibodies to Fc receptors on cells creates a problem that may challenge the interpretation of flow cytometric data. The use of nucleic acid ligand probes (having no Fc regions) may simplify this problem.

This application further describes flow cytometric methodologies. In general, flow cytometry is the analysis and optional sorting of particles, preferably cells, to which a fluorophore has been stoichiometrically bound. The analysis and sorting is based on various characteristics, including but not limited to, size, shape, granularity, and binding characteristics. The particles are passed through a beam of light and analyzed. The particles can further be sorted into one of two flasks depending on fluorescence or scatter characteristics. The particles are found in a substance which may or may not contain a target molecule of interest. When the substance itself is not necessarily particulate, the substance can be coated on a solid support, such as a bead, for use in flow cytometry.

Application in flow cytometry requires labelling a nucleic acid ligand with a fluorophore to produce a labelled nucleic acid ligand. The labelled nucleic acid ligand is contacted with a substance which may contain a target molecule, typically a heterogeneous population of cells, and allowed to form a labelled nucleic acid ligand: target complex when the target against which the nucleic acid ligand was evolved is present in the substance, typically on the surface of the cell or alternatively, the target may reside intracellularly. The labelled nucleic acid ligand: target complex is identified by the presence of the fluorescent label on the nucleic acid when the ligand:cell complex is analyzed by a flow cytometer.

The nucleic acid ligand is attached, either directly or through a linker, to a fluorophore. The fluorophore can be any one known in the art which includes, but is not limited to, fluorescein, rhodamine, Cy5 reactive dye, Cy3 reactive dye (both from Biological Detection Systems, Inc., Pittsburgh, Pa.), allophycocyanin, peridinine chlorophyll-a protein (PerCP), phycoerythrin, and green fluorescein protein (GFP).

The optional linker group can be any suitable spacer moiety. Suitable linker groups are exemplified by PEG, polyvinyl alcohol, polyacrylates and polypeptides.

The linkage between the linker group and the nucleic acid optionally is cleavable, leaving the nucleic acid intact. Examples of suitable cleavable linkages include, but are not limited to, photochemically labile linkers, disulfides, and carbonates. The linkage can also be cleavable with enzymes, such as DNAse and proteinases.

For certain flow cytometric applications where the amplification of the signal is necessary a second step staining of the primary nucleic acid ligand can be advantageous. Using biotinylated DNA and streptavidin-phycoerythrin (SA-PE), an oligonucleotide ligand can be equally amenable for the second step staining.

Another embodiment of the present invention provides a method for detecting the presence of a soluble target compound in a substance which may contain said target compound comprising a) immobilizing on a particulate solid support a capture molecule capable of binding to said target molecule; b) exposing a substance which may contain said target compound to said immobilized capture molecule to form a capture molecule:target molecule complex; c) adding to said capture molecule:target molecule complex a detector molecule capable of binding to said target molecule; and d) detecting said capture molecule:target molecule:detector molecule complex by flow cytometry; wherein said capture molecule, detector molecule or both are a nucleic acid ligand to said target molecule.

The capture molecule and/or the detector molecule must be a nucleic acid ligand to fall within the scope of the present invention. However, it is not required that both the capture molecule and the detector molecule be nucleic acid ligands. The ability of nucleic acid ligands to bind a target simultaneously with anti-target antibodies allows the development of a sandwich assay in which the nucleic acid ligand can be used as a capture and an anti-target antibody or a nucleic acid ligand can be used as a detector. In another embodiment, the nucleic acid ligand can be used as the detector molecule, with either a nucleic acid ligand or an antibody being used as the capture molecule. When either the capture molecule or the detector molecule is not a nucleic acid ligand it can be an antibody or other molecule that has specific recognition for the target molecule. In the most preferred embodiment of the invention, both the capture molecule and the detector molecule are nucleic acid ligands.

The capture molecule must bind to the target molecule to form a capture molecule:target molecule complex. The detector molecule must also bind to the target molecule, but additionally must comprise a detection system wherein a capture molecule:target molecule:detector molecule complex can be identified. The detector molecule comprises a detection system which comprises a wide array of known chemical entities which are applicable to flow cytometry, preferably fluorophores as described above.

Flow cytometry is a diagnostic tool which is predominately used in the research market, but also is used in clinical settings. The preferred use of the flow cytometry applications of the present invention is for the detection of target compounds for the clinical diagnosis of physiologic conditions. The labelled nucleic acid will most frequently be contacted with a substance which may contain a target compound and is then applied to a flow cytometer to determine whether any nucleic acid ligands bound to the target compound. The substance is usually a biological material which may or may not contain the target compound of interest. Such biological materials include blood, plasma, serum, sputum, urine, semen, cerebrospinal fluid, bronchial aspirate, and macerated tissue. Non-cellular biological material can be coated on beads for use in flow cytometry. The flow cytometry applications of the present invention are useful for both human and veterinary diagnostics. Other samples which may be assayed in the flow cytometry applications of the invention include foods and environmental discharges such as liquid wastes.

In Example 1, the present application is exemplified by using polystyrene beads coated with human neutrophil elastase (HNE) as the target and a DNA sequence that binds HNE with high affinity as the oligonucleotide ligand employed. The performance of the DNA ligand is compared to an anti-HNE antibody in detecting HNE on beads under flow cytometry conditions. Specifically, human neutrophil elastase coated on 3.3 micron beads and a high-affinity DNA ligand for HNE isolated by in vitro selection were used as a model to demonstrate the feasibility of using oligonucleotides, instead of, or in addition to, antibodies in flow cytometry. In this system, fluoresceinated DNA ligand is equally effective in detecting HNE beads as is fluoresceinated anti-HNE antibody.

In Example 2, an L-selectin ligand is used to determine whether L-selectin is on the surface of lymphocytes.

EXAMPLE 1

Detection of Human Neutrophil Elastase by Flow Cytometry

Materials & Methods

Spacer phosphoramidites that introduce an 18-atom spacer arm to oligonucleotides, Fluorescein-ON phosphoramidite and symmetric branching 3'—3' linking CPG were purchased from Clontech (Palo Alto, Calif.). Mouse anti-HNE antibody, was obtained from Dako Corp. (Carpinteria, Calif.). Rat anti-mouse $IgG_1$, clone X56 (from Becton Dickinson) was labeled with fluorescein isothiocyanate (FITC) to contain approximately one fluorescein per molecule of antibody. FLUORICON Polystyrene Assay Particles, 3.3 micron, were obtained from Baxter Healthcare (Mundelein, Ill.). HNE was bought as a salt-free lyophilized solid from Athens Research and Technology (Athens, Ga.). All other reagents were of analytical grade and were purchased from commercial sources. Enzymes were purchased from commercial sources.

Oligonucleotide Synthesis

Oligonucleotides containing fluorescein were chemically synthesized by standard solid phase chemistry using cyanoethyl phosphoramidites. Symmetric branching 3'—3' linking CPG was used to synthesize the tail-to-tail dimer via standard solid phase oligonucleotide synthesis procedures. After deprotection, DNA sequences were purified by denaturing polyacrylamide gel electrophoresis to ensure size homogeneity.

Preparation of HNE beads

Polystyrene beads were successively washed with PBS containing 0.1% SDS, PBS containing 0.01% TWEEN 20 and then with acetate buffer (50 mM NaOAc, 0.15M NaCl, pH 5.65). Beads (0.5% solids) in acetate buffer were coated with HNE (0.5 μg/cm² of bead surface area) for 30 min and then washed and suspended (approx. 5×10⁵ beads/μL) in acetate buffer containing 2% BSA. HNE coated beads were stored at 4° C. until use.

Flow Cytometry

Staining of HNE coated beads was achieved by incubating beads (approx. 3×10⁵) with varying concentrations of fluoresceinated oligonucleotides in 50 μL of binding buffer consisting of 100 mM Tris-HCl (pH 7.0), 0.15M NaCl, 6 mM KCl, 2 mM MgCl₂ and 1% BSA for 30 min at room temperature. The beads were then washed with 2 mL of the same buffer and suspended in 0.5 mL for analysis. Staining with mouse anti-HNE was accomplished in the same method except that bound antibody was detected by a second step fluorescein isothiocyanate (FITC) labeled antibody (X56-FITC). To obtain comparative measurements between the antibody and DNA (SEQ ID NOS: 2–8), X-56 was stoichiometrically labeled with FITC. Analysis was performed on a FACScan™ flowcytometer (Becton Dickinson). The sensitivity of the flowcytometer was adjusted so that the autofluorescence of the unstained beads was located in the middle of the first decade.

Measurements of Equilibrium Dissociation Constants ($K_d$)

DNA ligands containing fluorescein either near the 3' end or in the middle were radiolabeled at the 5' end with $^{32}$P-γ-ATP and T4 polynucleotide kinase. DNAs carrying fluorescein at the 5' end were radiolabeled with $^{32}$P-α-ddATP with terminal transferase. Radiolabeled DNAs were purified by denaturing polyacrylamide gel electrophoresis. Gel-purified DNAs resuspended at a final concentration of 1 nM in the standard binding buffer [150 mM NaCl, 100 mM Tris-HCl (pH 7.0), 2 mM MgCl₂ and 6 mM KCl] were heated to 70° C. for 3 min and cooled to room temperature to facilitate secondary structure formation.

Gel-purified radiolabeled DNA (<50 pM) were incubated with varying amounts of HNE in binding buffer containing 0.02% HSA (human serum albumin) for 10 min at 37° C. DNA-protein mixtures were filtered through prewet nitrocellulose filters (0.2 micron) and the filters were immediately washed with 5 mL binding buffer. The radioactivity retained on the filters was counted. Retention of DNA to filters in the absence of HNE, was determined and used for background correction. Assuming equimolar binding of DNA to HNE nonlinear least square method was used to fit the data by using the software package Kaleidagraph (Synergy Software, Reading, Pa.) to obtain equilibrium dissociation constant $K_d$.

Ligand binding to HNE on beads

Beads coated with HNE (10 μL) were incubated with varying amounts of end-labeled DNA in 100 μL of binding buffer at 37° C. for 10 min with brief mixing. To the binding reaction 0.5 mL of the binding buffer was added, mixed well, and the beads were spun in a picofuge to recover bead-bound DNA. After two additional washings, the radioactivity retained on the beads was counted by liquid scintillation. The $K_d$ was obtained as described above.

In flow cytometric analysis, $K_d$s were calculated by using the fluorescence signal plotted against the concentration of the fluoresceinated ligand.

Spectral and Fluorescent Measurements

The number of fluoresceins per oligonucleotide was determined spectrophotometrically. Extinction coefficient ε494= 7200M⁻¹cm⁻¹ was used for fluorescein both free in solution and tethered to DNA. DNA concentrations were based on ε₂₆₀ 13800, 6500, 10500 and 7900 M⁻¹cm⁻¹ for A, C, G and T, respectively. The relative quantum yield for each fluorescein labeled oligonucleotide was obtained by measuring the fluorescence (excitation 492 nm and emission 518 nm) in binding buffer relative to the fluorescence of a solution of fluorescein isothiocyanate (FITC). The concentration of each oligonucleotide was adjusted so that the absorption at 494 nm was approximately the same, and small differences from the absorbance of the reference FITC solution were normalized (fluorescence×gain−1×OD₄₉₄⁻¹).

Fluorescein Placement

A SELEX-derived 45 nt DNA sequence that bind HNE with high affinity ($K_d$=17 nm) and specificity was used as shown in Table I (SEQ ID NO: 1). Nucleic acid ligands to human neutrophil elastase are described in detail in co-pending patent application Ser. No. 08/199,507, filed Feb. 22, 1994, entitled Methods of Identifying "Nucleic Acid Ligands of Human Neutrophil Elastase," now U.S. Pat. No. 5,472,841 which is herein incorporated by reference in its entirety. NMR data and comparative sequence analysis of other members of the sequence family, supported the folding of the sequence into a G-quartet structure with duplex ends. Several constructs were made of the sequence containing either one or two fluorescein molecules as shown in Table I. Fluorescein was directly attached to either the 5' end or near the 3' end of the sequence to obtain DNA-5F (SEQ ID NO: 2) and DNA-3F (SEQ ID NO: 3), respectively. Due to the lack of commercially available CPG to introduce fluorescein at the 3' end, fluorescein was placed as a penultimate residue at the 3' end of DNA-3F. In DNA-LNK-5F (SEQ ID NO: 4) and DNA-LNK-3F (SEQ ID NO: 5) constructs, two additions of spacer phosphoramidite, each consisting of six ethylene glycol units, were placed between DNA and fluorescein at either 5' or 3' end, respectively. Two dimers of the sequence, each containing two fluorescein molecules, were also synthesized. These dimers were linked by ethylene glycol linkers in either head to tail (DNA-DIMER-HT) (SEQ ID NO: 6) or tail to tail orientation (DNA-DIMER-TT) (SEQ ID NO: 7). Complementary regions that base pair in the proposed structure were extended in DNA-EXT (SEQ ID NO: 8) and the extension contained two fluoresceins spaced by 7 nucleotides. This spacing is believed to prevent intrastrand fluorescence quenching.

Affinities and Specificity

Affinities of different DNA ligand constructs for HNE in solution were measured by nitrocellulose filter binding (Table 2). All constructs showed high-affinity binding for HNE, indicating that binding affinity was not affected by the attachment of fluorescein or ethylene glycol linker or both. In these constructs the two structural motifs of DNA proposed to involve in protein binding were not altered, explaining the retention of high-affinity binding to HNE. The two dimers, designed to investigate the effect on affinity upon dimerization of the sequence, bound somewhat better than the monomers. Out of all constructs, DNA-DIMER-HT had the lowest $K_d$ (0.5 nM), an order of magnitude better than the best monomeric form (DNA-3F).

The binding of DNA-LNK-3F and DNA-3F to HNE coated polystyrene beads detected by flow cytometric analysis is shown in FIGS. 1A–1D. Compared to beads alone (FIG. 1A showing autofluorescence of HNE beads), the addition of either ligand generated a clear change in signal (FIGS. 1B and 1C) analogous to the addition of an anti-HNE antibody (FIG. 1D). However, the fluorescence intensity differs between the two constructs; the signal produced by DNA-LNK-3F upon binding to HNE on beads is higher and in the same range as that of the antibody than the signal produced by DNA-3F. The only difference between these two constructs is the way in which fluorescein was linked. The construct that produced the signal intensity comparable to that of the antibody had fluorescein attached through an ethylene glycol tether.

FIG. 2 shows the intensities of fluorescence signals generated by different ligand constructs upon binding to HNE on beads plotted as a function of the ligand concentration. Based on this result, ligand constructs can be categorized into three groups; molecules that generate high, moderate and low signals. Constructs that gave high signal included a dimer (DNA-DIMER-TT) containing two fluorescein molecules and a monomer in which the fluorescein was attached near the 3' end by an ethylene glycol linker (DNA-LNK-3F). Monomeric forms in which fluorescein was directly attached either to the 5' (DNA-5F) or near the 3' end (DNA-3F) as well as DNA-EXT gave very poor signal in flow cytometry. Medium signal was produced by DNA-LNK-5F and the head-to-tail dimer. The data show that DNA constructs in which fluorescein was attached through an ethylene glycol linker have higher fluorescence signal intensities than constructs in which fluorescein was directly coupled to the sequence. In all cases, the signal saturates beyond certain concentration, allowing the calculation of the $K_d$ for each construct for binding to HNE on beads (Table 2). The observed $K_d$s for ligand binding to HNE on beads were generally lower than those obtained for binding to HNE in solution (Table 2).

The two $K_d$ measurements for ligand binding to HNE in solution and on beads were obtained by two different techniques. To determine whether the discrepancy is due to the two experimental approaches, the binding of two radiolabeled ligands (DNA-3F and DNA-LNK-3F) to HNE on beads was measured showing $K_d$s of 140 and 300 nM, respectively. The $K_d$s of these two ligands binding to HNE on beads measured by radioactivity were somewhat higher than those obtained by flow cytometry. The radioactivity measurement requires that the radioactivity retained by the total number of beads is measured as a function of the input DNA concentration. Thus, the measured value of radioactivity is very sensitive to the number of beads that survive after several washes. The small size of these beads (3.3 micron) makes them sensitive to washing, even under the most careful conditions. Conversely, in flow cytometry, the fluorescence of the number of beads counted is carefully controlled and that number is typically lower than the total number of beads used. This may explain the discrepancy of the results obtained by direct radioactivity measurements and flow cytometry.

In general, the $K_d$s of ligand binding to HNE on beads were higher than those obtained by filter binding technique (Table 2 & 3). Under filter binding conditions ligand binding site(s) on HNE should be well accessible since the protein is in solution. However, such site(s) may not be fully available once the protein is coated onto a solid surface (beads) and this may explain high $K_d$ values observed for ligand binding to the protein presented on beads.

Fluorescence Analysis in flow cytometry of various constructs do not correlate with their binding affinities nor do they correlate with the number or position of fluorescein in each construct. Therefore, the fluorescence characteristics of constructs (Table 3) were analyzed. Except for DNA-DIMER-TT, the experimental value of the average number of fluoresceins per oligonucleotide molecule was somewhat lower than the theoretical (or the expected) value for other ligand constructs. The two sets of constructs carrying fluorescein at the 5' or near the 3' end had similar number of fluoresceins per oligonucleotide. However, their relative quantum yields (RQY) were substantially different (0.93 for DNA-LNK-3F and 0.49 for DNA-3F; 0.67 for DNA-5F and 0.57 for DNA-LNK-5F). The two constructs that gave the highest fluorescence signal in flow cytometry had the highest RQY per oligonucleotide molecule. However, in other constructs the correlation between the signal intensity and the RQY per oligonucleotide did not agree well, suggesting that the fluorescence behavior of these molecules are rather complex. It is possible that upon interaction with the protein fluorophores, these constructs may find different local environments affecting the overall signal intensity.

Figure 3:
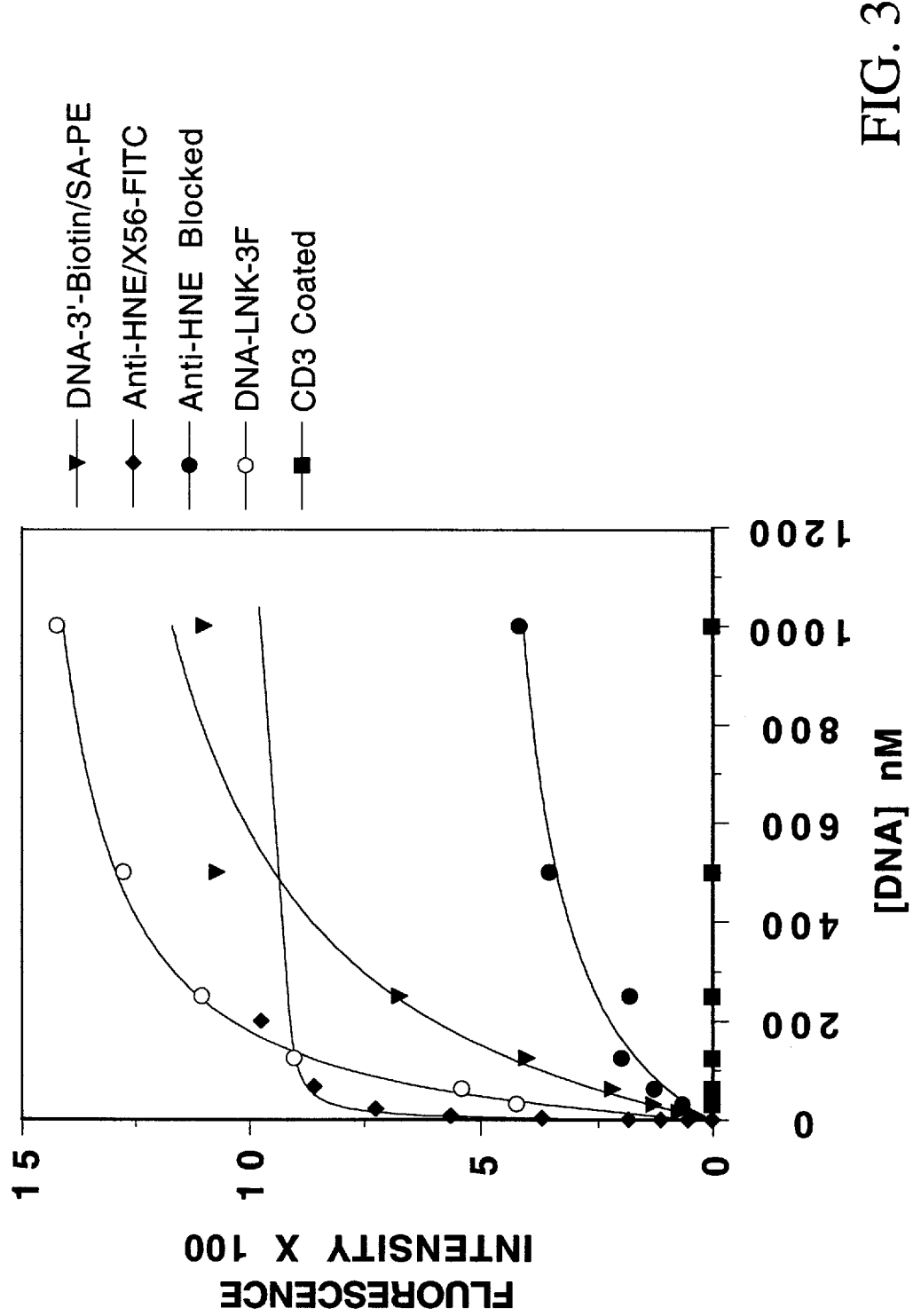
FIG. 3 shows the results of binding analysis of DNA-LNK-3F and anti-HNE monoclonal antibody to HNE on beads. Binding of DNA-LNK-3F either to HNE on beads in the absence of an antibody (open circles) or to HNE on beads that was preblocked with anti-HNE antibody (closed circles). The binding of the same ligand (DNA-LNK-3F) to CD3 coated beads is shown by squares. Triangles indicate the binding analysis of biotinylated DNA carried out by second step staining with streptavidin conjugated with phycoerythrin. Diamonds show the binding of anti-HNE antibody to HNE directly coated on beads analysed by second step staining with rat anti-mouse X-56 antibody labeled with fluorescein.

Flow cytometry was used to investigate whether the DNA ligand (DNA-LNK-3F) and anti-HNE antibody compete for binding to HNE on beads. As shown in FIG. 3, the DNA ligand showed significantly low binding to HNE beads that were preincubated with the antibody (closed circles) as compared to binding to HNE beads in the absence of the antibody (open circles). This result suggests that the binding sites of the DNA ligand and the antibody are the same or overlapping. The $K_d$ of the antibody for binding to HNE coated beads obtained by flow cytometry was 4 nM (diamonds; FIG. 3) and both DNA dimers had $K_d$s (under flow cytometry) of the same order of magnitude (15–20 nM; Table 1). As shown by closed squares (FIG. 3), HNE-specific DNA ligand did not bind to CD3-attached beads, indicating the target specificity.

The antibody binding data presented in FIG. 3 was obtained by a two step staining procedure, in which the HNE-bound anti-HNE antibody was stained with a fluoresceinated secondary antibody. The possibility of second step staining for oligonucleotide was investigated by using a biotinylated DNA ligand (biotin was attached to the 3' end through a linker) and streptavidin labeled with phycoerythrin (SA-PE). Triangles in FIG. 3 shows the saturation of PE signal as a function of concentration of biotinylated DNA demonstrating the feasibility of second step staining for oligonucleotide ligands as well. However, the affinity of biotinylated DNA binding to HNE measured by staining with SA-PE was lower than the direct fluorescence measurement of the same sequence (compare open circles and triangles). It is also important to note that the intensity of the PE signal observed in the experiment described in FIG. 3 is about 10-fold lower than its typical value.

Overall, the data of the model study presented here suggests that oligonucleotide-based high affinity ligands can be used as probes in flow cytometric applications.

EXAMPLE 2

Detection of L-Selectin by Flow Cytometry

L-selectin is a protein that is expressed on the surface of most leukocytes, particularly neutrophils and naive lymphocytes, under various physiological conditions. Therefore, the ability to determine the presence of L-selectin on the surface of certain cell types is clinically useful. Flow cytometry can be used to make such a determination by the procedures outlined by Picker, et al. (J. Immunol. (1993) 150:1105–1121). A ssDNA ligand to L-selectin is used as the labelled nucleic acid ligand. The ssDNA ligand was identified as described in concurrently filed U.S. patent application Ser. No. 08/479,724, filed Jun. 7,1995 entitled "High Affinity Nucleic Acid Ligands to Lectins," which is incorporated by reference herein in its entirety. The ssDNA ligand was termed #227 and had the following sequence: 5'CTAC-C T A C G A T C T G A C T A G C C G G A C A T-G A G C G T T A C A A G G T G C T A A A C GTAACGTACTTGCTTACTCTCATGTAGTTCC-3' (SEQ ID NO: 9). The nucleic acid ligand was labelled and used in flow cytometry in place of an antibody as described by Picker et al., supra or as described in Example 1.

TABLE 1

| SEQ ID NO: | Name | Sequence |
|---|---|---|
| 1 | PARENT | 5'-TAGCGATACTGCGTGGGTTGGGGCGGGTAGGGCCAGCAGTCTCGTT-3' |
| 3 | DNA-3F | 5'-TAGCGATACTGCGTGGGTTGGGGCGGGTAGGGCCAGCAGTCTCGT<u>FT</u>-3' |
| 5 | DNA-LNK-3F | 5'-TAGCGATACTGCGTGGGTTGGGGCGGGTAGGGCCAGCAGTCTCGT<u>LLFT</u>-3' |
| 2 | DNA-5F | 5'-<u>FT</u>AGCGATACTGCGTGGGTTGGGGCGGGTAGGGCCAGCAGTCTCGT-3' |
| 4 | DNA-LNK-5F | 5'-<u>FLL</u>TAGCGATACTGCGTGGGTTGGGGCGGGTAGGGCCAGCAGTCTCGT-3' |
| 7 | DNA-DIMER-TT | 5'-TAGCGATACTGCGTGGGTTGGGGCGGGTAGGGCCAGCAGTCTCGT<u>LFLXLFL</u>TGCTCTGACGACCGGGATGG-GCGGGGTTGGGTGCGTCATAGCGAT-5' |
| 6 | DNA-DIMER-HT | 5'-TAGCGATACTGCGTGGGTTGGGGCGGGTAGGGCCAGCAGTCTCGT<u>LFLFL</u>TAGCGATACTGCGTGGGTTG-GGGCGGGTAGGGCCAGCAGTCTCGT-3' |
| 8 | DNA-EXT | 5'-GFCACAGTCGACGATACTGCGTGGGTTGGGGCGGGTAGGGCCAGCAGTCTCGT<u>F</u>GACTGTGTC-3' |

TABLE 2

| | | Kd (nM) | |
|---|---|---|---|
| SEQ ID NO: | DNA Ligand Construct | Filter binding¶ | Flow cytometry |
| 2 | DNA-5F | 13 ± 4 | 154 ± 53 |
| 3 | DNA-3F | 6.6 ± 2 | 120 ± 22 |
| 4 | DNA-LNK-5F | 12 ± 6 | 110 ± 23 |
| 5 | DNA-LNK-3F | 17.5 ± 4 | 90 ± 2 |
| 6 | DNA-DIMER-HT | 0.5 ± 0.2 | 15 ± 3 |
| 7 | DNA-DIMER-TT | 3 ± 1.5 | 20 ± 4 |
| 8 | DNA-EXT | 12 ± 3 | 48 ± 10 |

TABLE 3

| SEQ ID NO: | Ligand Construct | F/Oligomer | RQY/ | Detected Fluorescence* | RQY/Oligomer |
|---|---|---|---|---|---|
| 2 | DNA-5F | 0.6 | 0.67 | 39 | 0.42 |
| 3 | DNA-3F | 0.7 | 0.49 | 92 | 0.34 |
| 4 | DNA-LNK-5F | 0.6 | 0.57 | 396 | 0.34 |
| 5 | DNA-LNK-3F | 0.7 | 0.93 | 1440 | 0.69 |
| 6 | DNA-DIMER-HT | 1.7 | 0.22 | 652 | 0.38 |
| 7 | DNA-DIMER-TT | 2.0 | 0.32 | 1431 | 0.64 |
| 8 | DNA-EXT | 1.3 | 0.25 | 283 | 0.33 |

We claim:

1. A method for detecting the presence of a target compound in a substance which may contain said target compound, wherein said target compound or said substance is particulate, comprising:

a) identifying a nucleic acid ligand from a candidate mixture of nucleic acids, said nucleic acid ligand being a ligand of said target compound, by the method comprising:
      i) contacting the candidate mixture with said target compound, wherein nucleic acids having an increased affinity to said target compound relative to the candidate mixture may be partitioned from the remainder of the candidate mixture;
      ii) partitioning the increased affinity nucleic acids from the remainder of the candidate mixture;
      iii) amplifying the increased affinity nucleic acids to yield a ligand-enriched mixture of nucleic acids; and
      iv) identifying said nucleic acid ligand;
   b) attaching said nucleic acid ligand with a fluorophore to form a fluorophore-labelled nucleic acid ligand;
   c) mixing said fluorophore-labelled nucleic acid ligand with a substance which may contain said target compound under conditions suitable for binding of the fluorophore-labelled nucleic acid ligand to said target compound; and
   d) analyzing said mixture by flow cytometry to detect whether said fluorophore-labelled nucleic acid ligand bound to said target compound in said substance, whereby the presence of a target compound in a substance can be detected.

2. The method of claim 1 wherein said fluorophore of said fluorophore labelled nucleic acid ligand is selected from the group consisting of fluorescein, rhodamine, Cy5 reactive dye, Cy3 reactive dye, allophycocyanin, peridinine chlorophyll-a protein (PerCP), phycoerythrin, and green fluorescein protein (GFP).

3. The method of claim 1 wherein said substance is a biological fluid.

4. The method of claim 1 wherein said substance comprises cells.

5. The method of claim 3 wherein said substance is selected from the group consisting of blood, plasma, serum, sputum, urine, semen, cerebrospinal fluid, bronchial aspirate, and macerated tissue.

6. The method of claim 5 wherein said substance is selected from the group consisting of blood, plasma, serum and macerated tissue.

7. The method of claim 1 wherein said target compound is on the surface of a cell.

8. The method of claim 1 wherein said target compound is intracellular.

9. The method of claim 8 wherein said target compound is cytoplasmic.

10. The method of claim 1 wherein unbound fluorophore-labelled nucleic acid ligand is removed from said mixture between steps c) and d).

11. A method for detecting the presence of a soluble target compound in a substance which may contain said target compound by flow cytometry comprising:
   a) immobilizing on a particulate solid support a capture molecule capable of binding to said target compound;
   b) exposing a substance which may contain said target compound to said capture molecule;
   c) adding to said capture molecule:target compound complex a fluorophore-labelled detector molecule capable of binding to said target compound; and
   d) detecting said capture molecule:target compound:detector molecule complex by flow cytometry, wherein said capture molecule, detector molecule or both are a nucleic acid ligand to said target compound, wherein said nucleic acid ligand is identified by the method comprising:
      i) preparing a candidate mixture of nucleic acids:
      ii) contacting the candidate mixture with said target compound, wherein nucleic acids having an increased affinity to said target compound relative to the candidate mixture may be partitioned from the remainder of the candidate mixture;
      iii) partitioning the increased affinity nucleic acids from the remainder of the candidate mixture,
      iv) amplifying the increased affinity nucleic acids to yield a ligand-enriched mixture of nucleic acids, and
      v) identifying said nucleic acid ligand.

12. The method of claim 11 wherein said particulate solid support is a bead.

13. The method of claim 11 wherein steps b) and c) are done simultaneously.

14. A method for detecting the presence of a non-nucleic acid target compound in a substance which may contain said non-nucleic acid target compound, wherein said non-nucleic acid target compound or said substance is particulate, comprising mixing said substance with a fluorophore labelled nucleic acid ligand which is capable of binding to said non-nucleic acid target compound and analyzing said mixture by flow cytometry to detect whether said fluorophore labelled nucleic acid ligand bound to said non-nucleic acid target compound in said substance, whereby the presence of a non-nucleic acid target compound in a substance can be detected, wherein said nucleic acid ligand is identified by the method comprising:
   a) preparing a candidate mixture of nucleic acids;
   b) contacting said candidate mixture of nucleic acids with said target compound, wherein nucleic acids having an increased affinity to said target compound relative to the candidate mixture may be partitioned from the remainder of the candidate mixture;
   c) partitioning the increased affinity nucleic acids from the remainder of the candidate mixture;
   d) amplifying the increased affinity nucleic acids to yield a ligand-enriched mixture of nucleic acids; and
   e) identifying said nucleic acid ligand.

* * * * *

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 1:
        TAGCGATACT GCGTGGGTTG GGGCGGGTAG GCCAGCAGT CTCGTT    46

( 2 ) INFORMATION FOR SEQ ID NO: 2:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: N at position 1 is fluorescein ( x i ) SEQUENCE DESCRIPTION: SEQ ID NO: 2:
        NTAGCGATAC TGCGTGGGTT GGGGCGGGTA GGGCCAGCAG TCTCGT    46

( 2 ) INFORMATION FOR SEQ ID NO: 3:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: N at position 46 is fluoresc ( x i ) SEQUENCE DESCRIPTION: SEQ ID NO: 3:
        TAGCGATACT GCGTGGGTTG GGGCGGGTAG GGCCAGCAGT CTCGTNT    47

( 2 ) INFORMATION FOR SEQ ID NO: 4:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: N at position 1 is fluorescein ( i x ) FEATURE:
        ( D ) OTHER INFORMATION: N at position 2 and 3 is six eth ( x i ) SEQUENCE DESCRIPTION: SEQ ID NO: 4:
        NNNTAGCGAT ACTGCGTGGG TTGGGGCGGG TAGGGCCAGC AGTCTCGT    48

( 2 ) INFORMATION FOR SEQ ID NO: 5:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: N at position 46 and 47 is six
        ethylene glycol units ( i x ) FEATURE:
        ( D ) OTHER INFORMATION: N at position 48 is flouresc ( x i ) SEQUENCE DESCRIPTION: SEQ ID NO: 5:
        TAGCGATACT GCGTGGGTTG GGGCGGGTAG GGCCAGCAGT CTCGTNNNT    49

( 2 ) INFORMATION FOR SEQ ID NO: 6:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: N at position 46, 48 and 50 is
        six ethylene glycol units ( i x ) FEATURE:
        ( D ) OTHER INFORMATION: N at position 47 and 49 is flu ( x i ) SEQUENCE DESCRIPTION: SEQ ID NO: 6:
        TAGCGATACT GCGTGGGTTG GGGCGGGTAG GGCCAGCAGT CTCGTNNNNN    50
        TAGCGATACT GCGTGGGTTG GGGCGGGTAG GGCCAGCAGT CTCGT    95

( 2 ) INFORMATION FOR SEQ ID NO: 7:

( i ) SEQUENCE CHARACTERISTICS:

-continued

```
            ( A ) LENGTH: 97 base pairs
            ( B ) TYPE: nucleic acid
            ( C ) STRANDEDNESS: single
            ( D ) TOPOLOGY: linear (ii)
                    MOLECULAR TYPE: DNA ( i x ) FEATURE:
            ( D ) OTHER INFORMATION: N at position 46, 48, 50 and 52

( i x ) FEATURE:
            ( D ) OTHER INFORMATION: N at position 47 and 51 is flu ( i x ) FEATURE:
            ( D ) OTHER INFORMATION: N at position 49 is a glycerol
                    backbone used in symmetric branching CPG ( x i ) SEQUENCE DESCRIPTION: SEQ ID NO:7:
            TAGCGATACT   GCGTGGGTTG   GGGCGGGTAG   GGCCAGCAGT   CTCGTNNNNN        50
            NNTGCTCTGA   CGACCGGGAT   GGGCGGGGTT   GGGTGCGTCA   TAGCGAT           97

( 2 ) INFORMATION FOR SEQ ID NO: 8:

( i ) SEQUENCE CHARACTERISTICS:
            ( A ) LENGTH: 63 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( D ) OTHER INFORMATION: N at position 2 and 54 is flu ( x i ) SEQUENCE DESCRIPTION: SEQ ID NO: 8:
            GNCACAGTCG   ACGATACTGC   GTGGGTTGGG   GCGGGTAGGG   CCAGCAGTCT        50
            CGTNGACTGR   GTC                                                      63

( 2 ) INFORMATION FOR SEQ ID NO: 9:

( i ) SEQUENCE CHARACTERISTICS:
            ( A ) LENGTH: 79 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO: 9:
            CTACCTACGA   TCTGACTAGC   CGGACATGAG   CGTTACAAGG   TGCTAAACGT        50
            AACGTACTTG   CTTACTCTCA   TGTAGTTCC                                   79
```